United States Patent

Rossi

Patent Number: 5,472,614
Date of Patent: Dec. 5, 1995

[54] DIALYSIS MACHINE WITH SAFETY MONITORING AND A CORRESPONDING METHOD FOR MONITORING SAFETY

[75] Inventor: Andrea Rossi, Mantova, Italy

[73] Assignee: Hospal Ltd., Basel, Switzerland

[21] Appl. No.: 104,157

[22] PCT Filed: Dec. 28, 1992

[86] PCT No.: PCT/EP92/02999

§ 371 Date: Aug. 20, 1993

§ 102(e) Date: Aug. 20, 1993

[87] PCT Pub. No.: WO93/12827

PCT Pub. Date: Jul. 8, 1993

[30] Foreign Application Priority Data

Dec. 30, 1991 [IT] Italy .................. TO91A1047

[51] Int. Cl.⁶ .................................................. B01D 61/32
[52] U.S. Cl. ........................ 210/646; 210/85; 210/96.2; 210/143; 364/413.02; 604/4
[58] Field of Search ...................... 364/413.01, 413.02, 364/413.07, 550, 552, 579, 580; 210/85, 143, 321.71, 739, 646, 929, 96.2; 604/4–6

[56] References Cited

U.S. PATENT DOCUMENTS 3,946,731  3/1976  Lichtenstein .................. 210/929
4,370,983  2/1983  Lichtenstein .................. 210/929
5,247,434  9/1993  Peterson et al. ............... 364/188

FOREIGN PATENT DOCUMENTS 432138  6/1991  European Pat. Off. ........ 364/413.07

*Primary Examiner*—Joseph W. Drodge
*Attorney, Agent, or Firm*—Finnegan, Henderson, Farabow, Garrett & Dunner

[57] ABSTRACT

A dialysis machine (1) includes dialysis equipment (4), a control unit (2) controlling normal operation of the machine, and a safety unit (3) for monitoring the machine with a view to the problem of patient safety. The control unit controls actuators (6) and receives information from its own sensors (13). The safety unit is connected to the control unit and receives from it parameters relevant to safety which have been measured by the sensors (13) of the control unit and its own sensors (15) to receive values of the parameters and other parameters. If any abnormality is found in the parameters measured, the safety unit sends commands (SSR) relating to safe states which have to be established to the control unit (2) which controls the actuators (6) in a corresponding way. The condition of the actuators is monitored by the safety unit (3) which uses suitable sensors (17) to determine whether the actuators have carried out the required actions, and if not, Switches off the machine with its own actuators (8).

15 Claims, 3 Drawing Sheets

DIALYSIS MACHINE WITH SAFETY MONITORING AND A CORRESPONDING METHOD FOR MONITORING SAFETY

BACKGROUND OF THE INVENTION

1. Field of the Invention

This invention relates to a dialysis machine with safety monitoring and a corresponding method for monitoring safety.

2. Description of the Related Art

As is known, dialysis machines incorporate a dialysis unit which is connected to a patient by means of an extracorporeal circulation line and which is controlled by means of specific actuators by a control system which ensures that the most appropriate dialysis conditions for the treatment required are maintained at all times on the basis of the operator's settings and adjustments.

In order to ensure that the dialysis unit always operates correctly, a monitoring system is generally provided to check consistency between the set conditions and the actual conditions, to reveal any situations which are potentially hazardous to the patient and to generate corresponding commands for returning the machine to a non-hazardous situation. In a known dialysis machine both the control and monitoring functions are performed by a single processor. This arrangement is however disadvantageous in that it does not ensure a sufficient level of safety if there should be a fault in the processor, one of the sensors or one of the actuators. In order to overcome this problem and increase the safety of the machine, separate control and safety systems each provided with their own sensors and their own actuators, are provided in another known dialysis machine. This arrangement, according to which in practice all detection and actuation members are duplicated, in fact provides a sufficient level of safety, but at the cost of considerably greater structural complexity, which has a repercussion on the cost of the machine itself.

The object of this invention is therefore to provide a dialysis machine which overcomes the disadvantages of known machines, and in particular provides optimum safety in respect of possible faults, with a low system cost.

SUMMARY OF THE INVENTION

In accordance with this invention a dialysis machine is provided with safety monitoring comprising a dialysis unit, a plurality of control actuators for the said dialysis unit, a plurality of control sensors for measuring the control values of parameters which are of relevance to safety in the said dialysis unit, a control unit connected to the said control activators to send control signals and to the said control sensors to obtain the said control values, a safety unit connected to the said control unit and comprising means for generating commands capable of generating commands relating to safe states, and a plurality of safety sensors to measure the safety of values of the said parameters which are relevant to safety in the said dialysis unit, the said safety sensors being connected to the said safety unit, characterised in that the said safety unit comprises transmission means capable of sending the said commands relating to safe states to the said control unit, in that the said control unit includes means for sending activating signals corresponding to the said commands relating to safe states to the said control actuators, and in that the said control actuators are associated with a plurality of actuator sensors for measuring the operating parameters of the said control actuators, the said actuator sensors being connected to the said safety unit.

The invention also relates to a method for monitoring safety in a dialysis machine which incorporates the stages of:

sending the said commands relating to safe states from the said safety unit to the said control unit, generating actuation signals corresponding to the said commands relating to safe states by means of the said control unit, sending the said activating signals from the said control unit to control actuators, measuring operating parameters of the said control actuators and sending the said operating parameters to the said safety unit.

BRIEF DESCRIPTION OF THE DRAWINGS

For a better understanding of this invention a preferred embodiment will now be described purely by way of a non-restrictive example, with reference to the appended drawings, in which.

DESCRIPTION OF THE PREFERRED EMBODIMENTS

Figure 1:
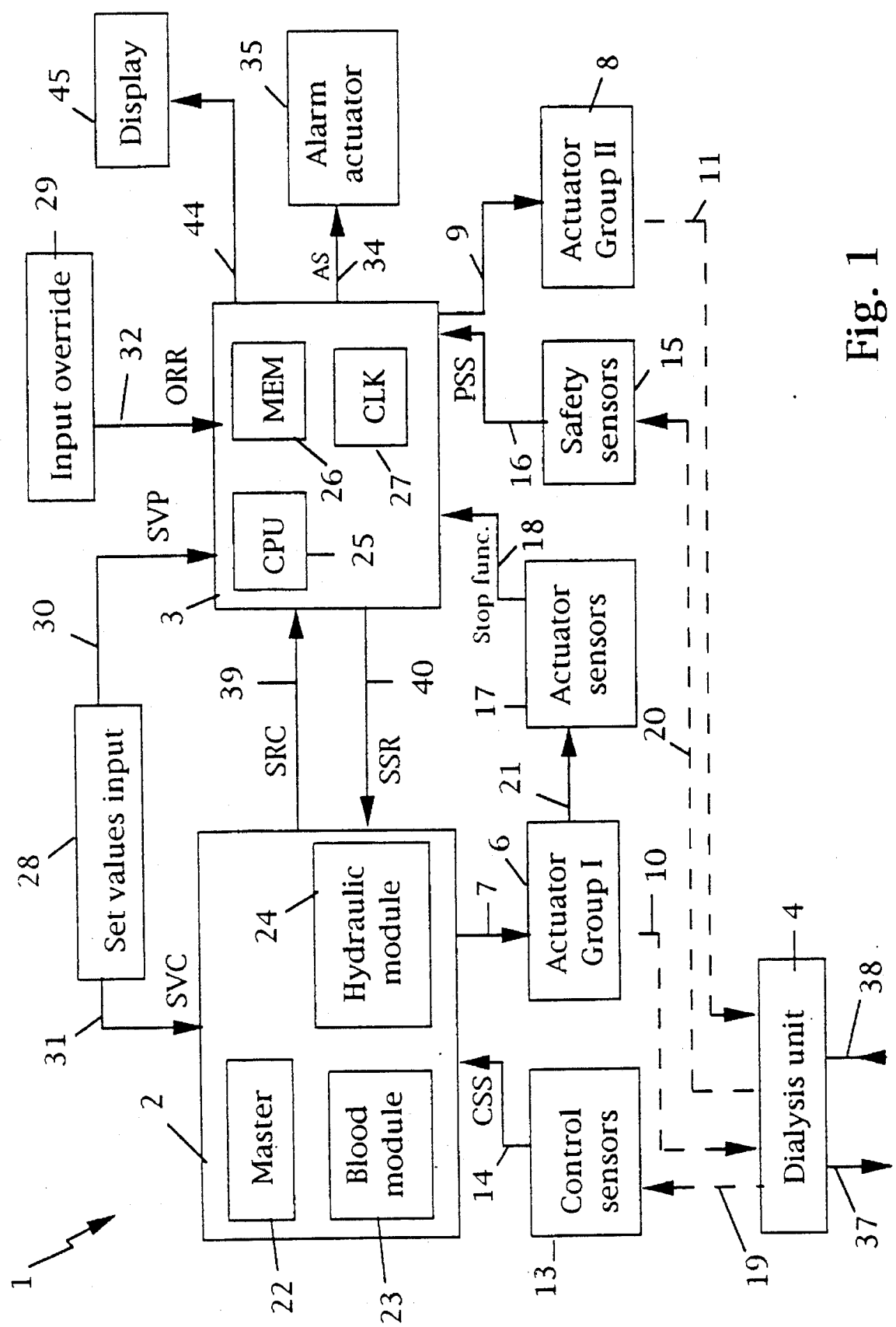
FIG. 1 is a simplified block diagram of a machine according to the present invention.

In FIG. 1 the dialysis machine, indicated as a whole by the number 1, is shown in simplified form so as to reveal only the parts of significance from the point of view of the safety of the machine itself. In particular, the control unit or system 2, the safety unit or system 3, a dialysis unit 4 and a plurality of actuators and sensors are shown in FIG. 1.

As illustrated, the actuators are divided into a first group, indicated by 6, connected to control unit 2 via incoming line 7, and include all the actuators necessary for carrying out dialysis treatment (e.g. pumps, valves, pressure regulators), added to a second group, indicated by 8 and connected to safety section 3 by ingoing line 9, which include all the actuators necessary for shutting down the machine and isolating the patient when a general safety condition is activated by safety unit 3 as will be described in greater detail below. The interactions between groups of actuators 6 and 8 and dialysis unit 4 are shown symbolically in FIG. 1 by dashed lines 10 and 11 respectively.

The sensors on the other hand are divided into three groups: a first group, indicated by 13 (control sensors), is connected to control unit 2 via outgoing line 14 to which the sensors provide CSS signals corresponding to the values which they have measured of the parameters of significance to safety (CRC signals) and the measured values of other characteristic parameters (such as flow and speed) which determine the progress of dialysis treatment. A second group, indicated by 15 (safety sensors), is connected to safety unit 3 via outgoing line 16 to which the sensors 15 provide PSS signals corresponding to the values which they have determined for the said parameters measured by sensors 13 and other parameters which are relevant to safety (SRP signals) and a number of items of information which are necessary to check that the safety unit itself is functioning correctly; and a third group, indicated by 17 (actuator sensors) is connected to safety unit 3 via outgoing line 18 to provide the latter with the values which these have determined of the operating parameters of actuators 6 set by control unit 2. In general therefore some of control sensors 13 (and more specifically those which measure parameters relevant to safety in dialysis unit 4) are duplicated by safety sensors 1S, for reasons which will become apparent below. The interaction between control sensors and safety sensors 13, 15 with dialysis unit 4 and between actuator sensors 17 and actuators 6 is shown symbolically in FIG. 1 by dashed lines 19, 20 and 21 respectively.

Control unit 2, which sets and adjusts the parameters and quantities required for correct performance of the dialysis treatment consists of three parts: a master 22 supervising control unit 2 and communicating with safety unit 3, a blood module 23 and a hydraulic module 24 which, under control of the master, generate the specific commands to the parts of dialysis unit 4 which are involved with the flow of blood and the flow of dialysis fluid respectively and which will not be described in detail as they are not pertinent to this invention.

Safety unit 3, which monitors conditions in relation to the problem of machine safety in relation to the patient, in turn comprises a CPU processing unit 25, a memory 26 and a clock CLK 27. Safety unit 3 is connected with two inputs 28 and 29, of which unit 28 is capable of receiving the initial set values SVP and SVC, e.g. following manual inputting by an operator, and of passing these via lines 30 and 31 to safety unit 3 and control unit 2 respectively, while unit 29 receives the requests for manual intervention by the operator in an alarm situation and generates a corresponding signal (override signal ORR) passed to safety unit 3 along line 32. Also safety unit 3 is connected by outgoing line 34 to an alarm actuator 35 (e.g. an illuminated and/or acoustic alarm) to indicate to the operator that an alarm condition exists, and via an outgoing line 44 to a screen 45 for the display of messages to the operator.

Dialysis unit 4 in which a patient's blood is dialysed incorporates all the physical components (apart from the actuators, which are shown separately) necessary for performing the dialysis itself, and can be connected to a patient who is to undergo dialysis via extracorporeal circulation lines 37, 38 which enter and leave dialysis unit respectively.

Control unit 2 and safety unit 3 exchange information and instructions, as explained in detail below, via a pair of lines 39, 40, and specifically line 39, which leaves control unit 2, is used by the latter to pass the values of the parameters relevant to safety (SRC signals) measured by its own sensors 13 to safety unit 3, while line 40, which leaves safety unit 3, is used by the latter to send the necessary instructions for implementing a safety state (SSR signals) to monitoring unit 2, as will be seen below.

Safety unit 3 of dialysis machine 1 according to the invention is designed to cope with all the anomalous situations which might endanger the patient, placing the machine in a safe condition as defined by the standard established by the approval authorities. With this object the safety system is brought into action as a result of which the safety unit receives as inputs all the parameters necessary for carrying out periodical monitoring (safety-relevant parameters) and checks that these parameters are consistent and that no unforeseen situation is obtained. If an anomaly should occur, after any transitory disturbance conditions have been ruled out, the safety unit determines what state the machine should be in so as not to constitute a hazard to the patient, and sends control unit 2 commands in respect of the actions which must be carried out by the actuators to overcome the situation (commands relating to a safe state). Control unit 2 processes these commands through master 22 and blood and hydraulic modules 23, 24 and generates corresponding control instructions for its own actuators. The actions corresponding to these control instructions, as carried out by control actuators 6, are monitored by actuator sensors 17 which send the corresponding signals to safety unit 3. Safety unit 3 then checks that these actions have been performed correctly, after a predetermined period which allows time for all the components involved to carry out the necessary operations. If the outcome of the check is favorable the machine remains in the safe condition until the cause which gave rise to the alarm is corrected (i.e. until the periodical test yields a negative result). If the outcome of the check is negative it is assumed that the machine is suffering a significant functional problem due to a fault in control unit 2 or actuators 6 or sensors 17. In this situation dialysis machine 1 is no longer in a position to operate reliably and there is a risk to the patient. As a consequence safety unit 3 generates a general safe condition activating its own safety actuators 8 so as to prevent dialysis fluid from flowing through the haemodialysis filter, shutting down the ultrafiltration pump, shutting down the blood module pump and preventing blood from re-entering the vein. In this way the machine is shut down and the patient is isolated.

Figure 2:
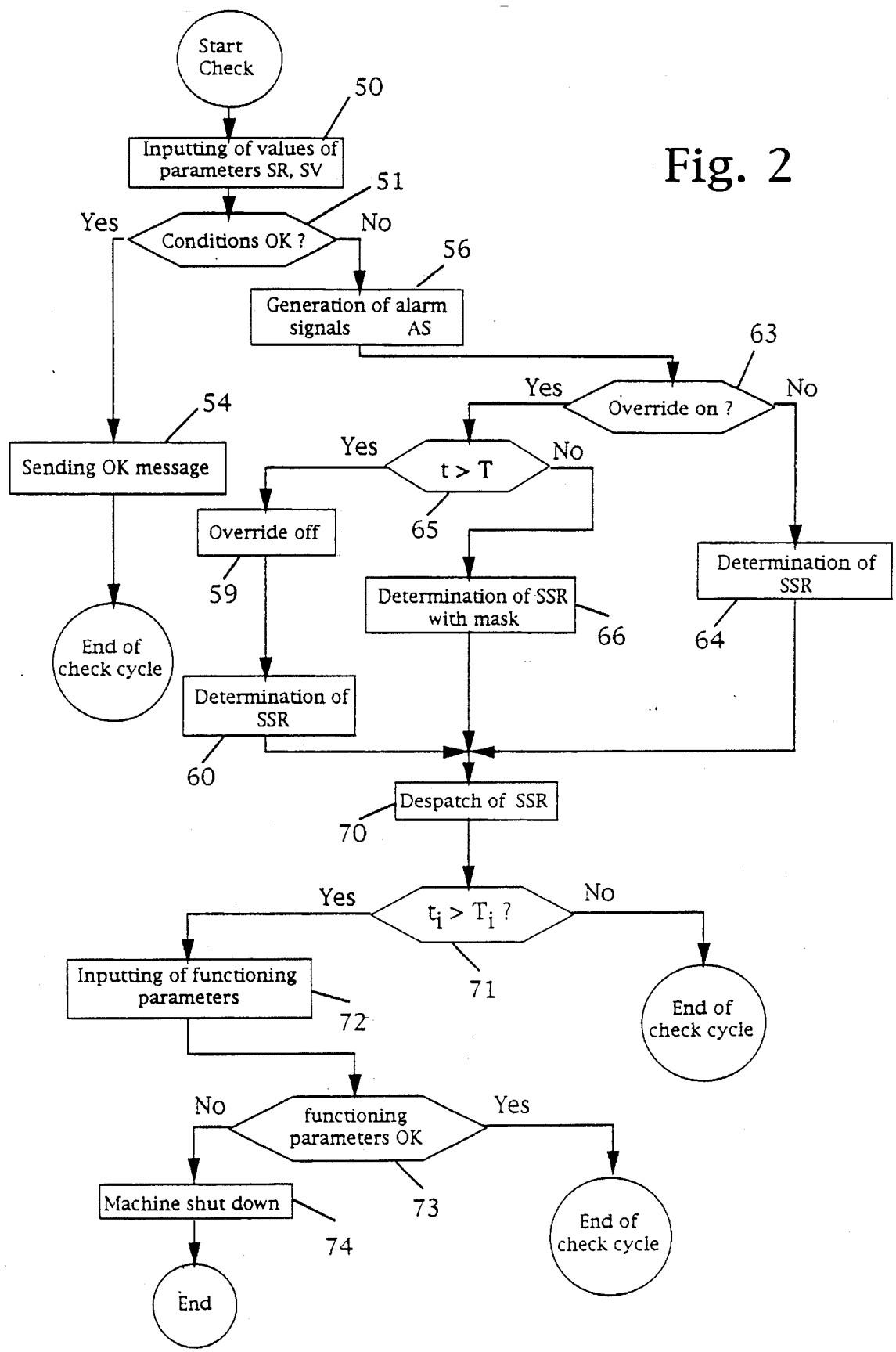
FIG. 2 is a first flow diagram relating to a method of safety monitoring implemented by the machine in FIG. 1.

The performance of the periodical test will now be described in greater detail with reference to FIG. 2. As is known, after the periodical test has been initiated safety unit 3 receives the values for the safety relevant parameters SR (SRC from the control unit and SRP from the safety unit) measured by sensors 13 and 15 and the SV values input by the operator (block 50) and then (block 51) checks that these values are consistent and meet predetermined conditions stored in its memory 26. In particular the safety unit carries out a specific check for each condition which has to be checked. In general the checking of a condition consists of checking a directly measurable parameter (such as e.g. the temperature of the dialysate or venous pressure), but may also include an evaluation of different parameters and their mutual relationships (such as in the case of biofiltration flow, which requires among other things a check to ensure that the ratio between the signal provided by the infusion pump position sensor and the signal relating to the position of the encoder teeth for that pump is correct). If the check is satisfactory (YES output from block 51) safety unit 3 cancels the alarm message previously sent to the operator by screen 45 (block 54). The periodical test is then concluded.

Vice versa, if an anomalous condition is found in one or more of the checks (an excessive difference between the SRC and SRP values recorded by sensors 13 and 15, or between the measured and set values for SV, or incorrect correlations between any of the measured parameters), safety unit 3 sends alarm signal AS to corresponding actuator 35 (block 56) and checks whether an override request is present (block 63). This override procedure allows the operator to intervene manually, effecting a maximum reduction in the specific configurations required from the machine when an anomaly exists, and may only be maintained for a predetermined period of time T. If the operator has not activated the override request (by the ORR signal in FIG. 1, NO output from block 63) a safe condition request SSR, (block 64), is generated, otherwise (YES output) a check is made to see if this override request is present for a time t which is greater than predetermined time T (block 65). For this purpose, and in asynchronous manner which is not illustrated, on receiving the ORR signal the safety unit activates a specific counter whose content is indicative of time t. If the override request has already been present for a time greater than T (YES output from block 65) then the system passes to block 59 in which the override request is deactivated in a manner which will be described in greater detail with reference to FIG. 4.

If instead the override request has been present for a time t less than predetermined time T (NO output from block 65) the system passes to block 66 in which the safety unit generates a stand-by safe condition, i.e. one in which the specific safety configurations requested by safety unit 3 are reduced to the maximum extent (in any event in accordance with the standards). This enables the operator to act on dialysis unit 4 to remove the cause which brought about the alarm.

After generating the request for a safe condition, whether stand-by or not, the safety unit sends it to control unit 2 along line 40 (block 70) and then checks that a time Ti since the sending of that request (block 71), which is characteristic for each specific state in the SSR request, has expired. As already indicated, this check is provided to ensure that machine 1 has sufficient time to react to the request.

Figure 3:
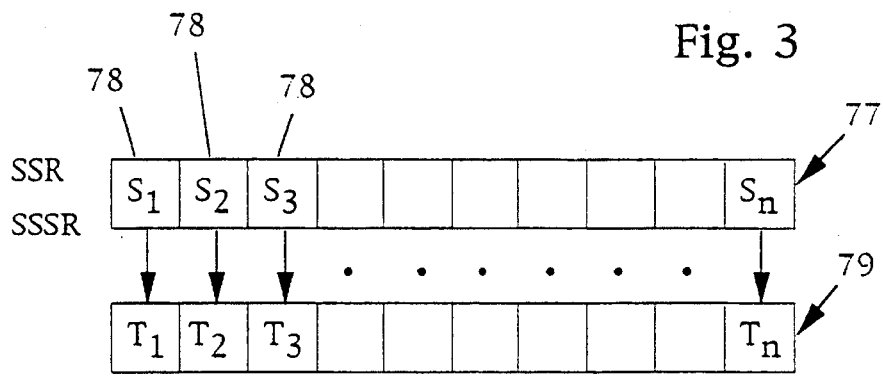
FIG. 3 is a second flow diagram relating to a method of safety monitoring implemented by the machine in FIG. 1.

To clarify this point, reference is first made to FIG. 3, which shows the format of SSR request and the specified associated execution times. As will be noted, each SSR request comprises a vector 77 subdivided into several fields 78, each of which stores in memory the condition, indicated by $S_1, S_2, \ldots, S_n$, which must be adopted by a corresponding control quantity or parameter for actuators 6. Individual fields 78 of vector 77 may be empty, in which case the corresponding quantities do not need to be altered. In any event a value $T_1, T_2, \ldots, T_i$ which specifies the time allowed for executing the commands associated with each state $S_i$ is associated with each state, as shown diagrammatically in FIG. 3 by vector 79.

The format of the overall SSR safe condition request shown in FIG. 3 is also common to individual specific safe condition requests SSSR, each of which is associated with a specific anomaly (anomalous condition in the sense indicated above). The SSR request thus results from the sum of all the requests for specific safe conditions, resolving any incompatibilities which may arise, as will be explained below with reference to the flow diagram in FIG. 4.

As a consequence, if the safe condition requests for all conditions $S_i$ are sent in a time $t_i < T_i$, the safety unit ends the test in progress. In subsequent tests safety unit 3 checks if any new alarms are present relating to conditions different from those which caused the first SSR request to be sent, and checks if an override request has been activated. The existence of only one of these two situations would naturally result in a change in the request for the safe condition and possibly in the initialising of the counters (not shown) which are associated with each new conditions $S_i$ and which count the time from the sending of the SSR including any new condition $S_i$, failing which the same request is maintained.

As soon as the time $T_i$ specified for a specific condition among the $S_i$ conditions requested has passed (YES output from block 71), safety unit 3 obtains the values of the operating parameters set by control unit 2 specified by that specific condition $S_i$ (block 72) from sensors 17 and checks that these are correct (block 73). If the parameters are correct (YES output from block 73), demonstrating that the machine 1 is operating correctly, the test cycle carried out at that time is terminated.

If instead after period of time $T_i$ provided by the specific condition for carrying out the orders resulting from the safe condition imposed the functional parameters relating to their specific condition have not reached their correct values (NO output from block 72), then safety unit 3 generates a general safe condition (block 74), sending the appropriate commands to its own safety actuators 8 so as to ensure that the commands are carried out independently of the condition of the rest of the machine.

Figure 4:
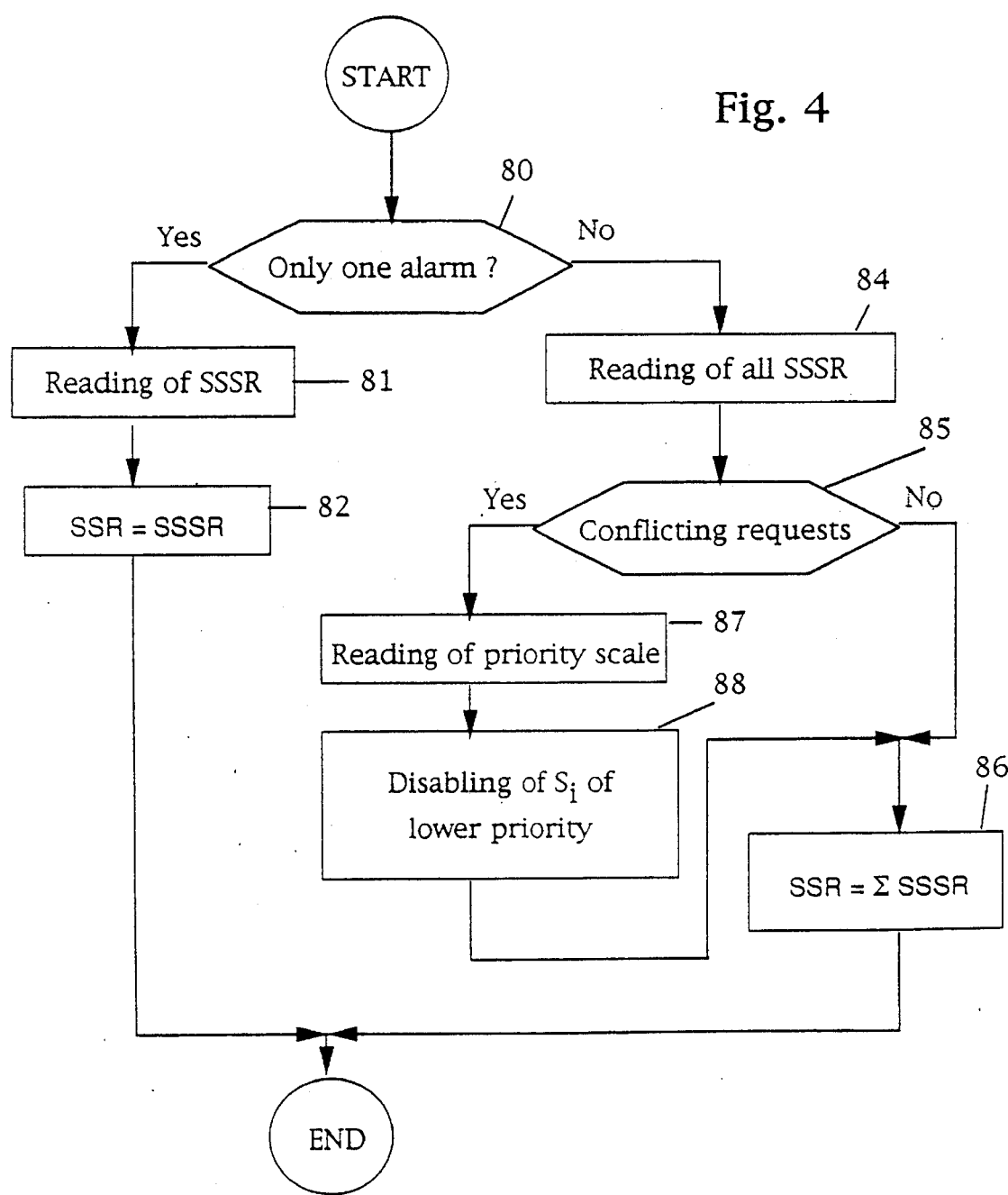
FIG. 4 is a diagram illustrating the passage of commands between the parts of the machine in FIG. 1 when an anomalous condition arises.

The generation of the request for a safe condition will now be described in greater detail with reference to FIG. 4. In that figure, when an alarm is present safety unit 3 checks whether a single anomalous condition is present (block 80). If this is the case (YES output from block 80), safety unit 3 reads vector 77 relating to a specific safe condition request SSSR (block 81) from its own memory 26 and then places vector SSR equal to vector SSSR which has been just read (block 82). If not (NO output from block 80) safety unit 3 reads the SSSR vectors corresponding to all anomalous conditions found (block 84), checks whether these vectors specify incompatible requests (block 85) and if this is not the case (NO output) generates vector SSR as the sum of the individual SSSR vectors which have just been read (block 86). If this is not the case (YES output from block 85) safety unit 3 reads a priority scale stored in memory 26 (block 87) and deactivates the commands associated with the condition or conditions $S_i$ of lower priority (block 88). Subsequently safety unit 3 determines the SSR vector in the way already described with reference to block 86. Obviously, and in a manner which is not illustrated in the figure, when an override request is present the SSR vector determined in this way is marked, in the sense that the fields relating to the parameters for which the operator specifies manual intervention are reduced to essentials by individual checks (in accordance with the standards).

The dialysis machine and the method of safety monitoring according to this invention have the following advantages. In the first place duplication of the components involved in safety monitoring is reduced to a minimum, and specifically it is restricted to the sensors which measure the safety relevant parameters (some of the sensors in group 13 and some of the sensors in group 15), as well as actuators 8 which are essential for shutting down the machine if a general safe condition request is present. As a consequence the construction and operating costs of the components are reduced to a minimum, without having an adverse effect on the service provided by the machine as regards its safety.

Both the machine and the corresponding method are extremely reliable and capable of coping with virtually all anomalous situations which arise, by attempting to overcome the specific anomaly or anomalies occurring, or in any event being in a position to shut down the machine in extreme circumstances.

Finally it is clear that modifications and variants which do not go beyond the scope of the invention itself may be made to the machine and method here described and illustrated. In particular it is emphasised that certain operations and functions can be carried out by a hierarchically superior processing system, instead of safety unit 3, which controls the safety unit in such a way as to take into account yet other parameters or quantities which are not directly correlated with the safety of the machine, or in any event to control certain functions in a centralised manner. In particular the controls on the duration of the override request and on the delay with which the parameters of actuators 6 is checked may be conveniently controlled at a higher level.

Also, instead of applying overall control to all anomalous conditions and then generating individual requests for safe conditions, it may be advantageous to provide a sequential chain, one for each condition which has to be checked, each of which comprises determination of the quantities required for a specific monitoring function, checking consistency, generating alarms and generating specific safe condition requests.

What is claimed is:

1. A system for providing monitored treatment to a patient, comprising:

a dialysis unit for providing treatment to a patient;

a first group of actuators adapted for operating the dialysis unit;

a second group of actuators operative for shutting off operation of the dialysis unit when the system is set to a general safe condition;

a control unit operative for controlling the first group of actuators in accordance with set values of control parameters, set values of safety parameters, and actual values of the safety parameters determined using a first group of sensors;

a safety unit operatively connected to the dialysis unit and operative for monitoring at regular intervals actual values of the safety parameters and for selectively setting the system in the general safe condition;

the first group of sensors being communicatively connected to the control unit and operative for providing the control unit with information indicative of both the actual values of the safety parameters and treatment progress parameters, wherein at least a subgroup of the first group of sensors provides, through the control unit, the actual values of the safety parameters to the safety unit;

a second group of sensors communicatively connected to the safety unit and operative for providing the safety unit with information indicative of the actual values of both the safety parameters and parameters indicative of an operative condition of the safety unit; and a third group of sensors communicatively connected to the safety unit operative for providing the safety unit with information indicative of an actual operative condition of the first group of actuators when the system is in the general safe condition, the third group of sensors being operative for communication with the safety unit in response to the safety unit detecting a patient endangering anomalous situation resulting from inconsistent information detected by one or more sensors of the first group or the second group.

2. The system according to claim 1, wherein the safety unit includes means for setting the system in the general safe condition in accordance with the actual values of the parameters indicative of an operative condition of the safety unit.

3. The system according to claim 1, wherein the safety unit includes means for setting the system in the general safe condition in accordance with the information indicative of an actual operative condition of the first group of actuators.

4. The system according to claim 1, wherein the safety unit includes means for receiving the set values of the control parameters.

5. The system according to claim 1, wherein the safety unit includes means for controlling the second group of actuators to shut off operation of the dialysis unit when the system is set in the general safe condition.

6. The system according to claim 1, further comprising an alarm actuator, connected to the safety unit, for producing an alarm upon occurrence of a preset alarm condition.

7. The system according to claim 1, further comprising an override unit connected to the safety unit for preventing the safety unit from setting the system in the general safe condition for a predetermined period of time upon command of an operator.

8. A method for monitoring a progressive extracorporeal blood treatment using a dialysis unit, a method comprising the steps of:

providing preset values of operating parameters and safety parameters;

treating a patient based on the preset values of the operating parameters and the safety parameters;

determining actual values of the operating parameters and the safety parameters using a first group of sensors;

determining actual values of the operating parameters and the safety parameters using a second group of sensors;

checking whether the actual values of the safety parameters determined using the first group of sensors are consistent with the preset values of the safety parameters and the actual values of the safety parameters determined using the second group of sensors;

setting the dialysis unit to a predetermined safety state when there exists an inconsistency between a preset safety parameter value, an actual safety parameter value determined using at least one of the first group of sensors, and an actual safety parameter value determined using at least one of the second group of sensors;

determining the treatment's progress based on actual values of operating parameters determined using a third group of sensors; and shutting off the dialysis unit at times when the treatment's progress does not reach a predetermined level.

9. The method according to claim 8, further comprising, the step of triggering at least a first alarm upon determining that the determined values of the safety parameters using the first group of sensors are not consistent with the preset values of the safety parameters.

10. The method according to claim 9, further comprising, the step of triggering a second alarm upon determining that the determined values of the safety parameters using the first group of sensors are not consistent with the determined values of the safety parameters using the second group of sensors.

11. The method according to claim 10, wherein the first alarm is associated with a first safety state and the second alarm is associated with a second safety state.

12. The method according to claim 11, further comprising, determining a priority between the first safety state and the second safety state upon triggering of at least two alarms, and setting the dialysis unit to the one having a higher priority of the first safety state and second safety state.

13. The method according to claim 9, further comprising the step of overriding at least the first alarm.

14. The method according to claim 8, wherein a predetermined period of time is caused to lapse before the step of determining the treatment's progress based on the determined values of the operating parameters using the third group of sensors and after the step of setting the dialysis unit to the safety state.

15. A system for providing monitored treatment to a patient, the system comprising:

a dialysis unit;

means for storing preset values of operating parameters and safety parameters;

means for controlling the dialysis unit to treat a patient based on the preset values of the operating parameters and the safety parameters;

a first group of sensors operative for determining actual values of the operating parameters, indicative of treatment progress, and the safety parameters;

a second group of sensors operative for determining actual values of the operating parameters and the safety parameters;

means for checking consistency between the actual values of the safety parameters determined using the first group of sensors, the preset values of the safety parameters, and the actual values of the safety parameters determined using the second group of sensors;

means for setting the dialysis unit to a predetermined safety state when the checking means detects an inconsistency between a preset safety parameter value, an actual safety parameter value determined using at least one of the first group of sensors, and an actual safety parameter value determined using at least one of the second group of sensors;

means for determining, when the dialysis unit is in the safety state, the treatment's progress based on actual values of operating parameters determined using a third group of sensors; and means for shutting off the dialysis unit at times when the treatment's progress does not reach a predetermined level.

* * * * *

UNITED STATES PATENT AND TRADEMARK OFFICE
CERTIFICATE OF CORRECTION

PATENT NO. : 5,472,614
DATED      : December 5, 1995
INVENTOR(S) : Andrea ROSSI

It is certified that error appears in the above-indentified patent and that said Letters Patent is hereby corrected as shown below:

Claim 1, column 7, line 41, before "operative" insert --and--.

Signed and Sealed this

Fourteenth Day of May, 1996

Attest:

BRUCE LEHMAN

Attesting Officer     Commissioner of Patents and Trademarks